United States Patent [19]

Sugiura et al.

[11] Patent Number: 5,728,573
[45] Date of Patent: Mar. 17, 1998

[54] TERMITICIDE AND METHOD FOR TERMITE CONTROL USING THE SAME

[75] Inventors: Masaaki Sugiura, Hiroshima-ken; Takashi Sugiyama, Hatsukaichi; Takeshi Saika, Ibaraki, all of Japan

[73] Assignee: Nitto Denko Corporation, Osaka, Japan

[21] Appl. No.: 611,575

[22] Filed: Mar. 6, 1996

[30] Foreign Application Priority Data

Mar. 7, 1995 [JP] Japan .................. 7-077406
Dec. 27, 1995 [JP] Japan .................. 7-353779

[51] Int. Cl.$^6$ .............. C12N 1/14; C12N 1/16; C12N 1/18; A01N 63/00
[52] U.S. Cl. ................ 435/254.1; 424/93.5; 435/260
[58] Field of Search .............. 424/93.5; 435/254.1, 435/260

[56] References Cited

U.S. PATENT DOCUMENTS 5,418,164  5/1995  Andersch et al. .............. 435/254.1
5,512,280  4/1996  Johal et al. ................... 424/93.5

FOREIGN PATENT DOCUMENTS 1-533177   7/1968   France .
63-258803  10/1988  Japan .
4-202104   7/1992   Japan .
9309672    5/1993   WIPO .

OTHER PUBLICATIONS

Kawakami, Bulletin of Sericultural Experiment Station (Tokyo), 27(4), pp. 445–467 (1978). Summary in English.
Proc. Assoc. Pl. Pro. Kyushu, 34:190–193 (1988). Abstract in English.
ATCC Catalogue of Filamentous Fungi 1991 18$^{th}$ ed. pp. 74–76.
Lai et al. J. Invert. Pathol. 1982. vol. 39 pp. 1–5.
Bao et al. Entomophaga. 1971. vol. 16(3) pp. 343–352.

*Primary Examiner*—Leon B. Lankford, Jr.
*Assistant Examiner*—Christopher R. Tate
*Attorney, Agent, or Firm*—Birch, Stewart, Kolasch & Birch, LLP

[57] ABSTRACT

A termiticide comprising an entomogenous fungus, such as *Beauveria brongniartii*, and/or a culture thereof; and a method for termite control using the termiticide.

14 Claims, No Drawings

1

TERMITICIDE AND METHOD FOR TERMITE CONTROL USING THE SAME

BACKGROUND OF THE INVENTION

1. Field of the Invention

The present invention relates to a termiticide containing an entomogenous fungus and/or a culture thereof, and to a method for termite control using the termiticide.

2. Discussion of the Related Art

Pesticides are usually used to control harmful insects. The use of pesticides is sometimes harmful to men and beasts. Therefore, attempts have been made to use a natural enemy for controlling harmful insects as a pesticide which is safe to men and beasts. Using a entomogenous fungus is one of such attempts. Japanese Patent Laid-Open Nos. 4-202104 and 63-258803 disclose the use of fungi to control a long-horned beetle.

For termite control, organophosphate and pyrethroid pesticides have widely been used in the forms of oil solution and emulsion, which are sprinkled over the ground or lumbers, or injected into the infested structures of lumber. Recently, however, there has been increasing concern about the influence of these chemical pesticides upon humans and beasts as well as upon the natural environment. Also, termiticides are usually applied to a narrow space such as a space under the floor and therefore present operational difficulties and health hazards to the workers.

SUMMARY OF THE INVENTION

An object of the present invention is to provide a termiticide and a method for termite control which give no harm to humans and beasts, less environmental influences, no difficulties in handling, and eradication of termites.

The present inventors made extensive studies to achieve the above object and found that fungi of certain types have a specific killing-activity against termites among arthropods including termites, cockroaches, ants, pill wood lice, sow bugs, large centipedes, and shield centipedes, and have completed the present invention.

Specifically, the gist of the present invention is concerned with:

(1) A termiticide comprising an entomogenous fungus and/or a culture thereof;

(2) The termiticide described in (1) above, wherein the entomogenous fungus is *Beauveria brongniartii*;

(3) The termiticide described in (1) above, wherein the entomogenous fungus is selected from the group consisting of *Beauveria bassiana, Beauveria amorpha, Metarhizium anisopliae*, and *Verticillium lecanii*;

(4) The termiticide described in any one of (1) to (3) above, wherein the entomogenous fungus is in the state of germination or resting spore;

(5) The termiticide described in any one of (1) to (4) above, wherein the entomogenous fungus and/or the culture thereof are contained in an application form selected from the group consisting of powder, granule, tablet, liquid, aerosol, band, sheet, pellets, and cream;

(6) The termiticide described in (5) above, wherein cell density of the entomogenous fungus in the application form is $10^5$ to $10^9$ cells/cm$^2$ or $10^5$ to $10^9$ cells/g;

(7) The termiticide described in any one of (1) to (6) above, wherein a target termite is selected from the group consisting of *Coptotermes sp., Reticulitermes sp., Cryptotermes sp., Incisitermes sp., Macrotermes sp.*, and *Odontotermes sp.*;

(8) The termiticide described in (7) above, wherein a target termite is selected from the group consisting of *Coptotermes formosanus, Reticulitermes speratus, Reticulitermes hesperus, Reticulitermes tibialis, Reticulitermes flavipes, Reticulitermes lucifugus, Reticulitermes santonensis, Cryptotermes domesticus*, and *Incisitermes minor*; and (9) A method for termite control using the termiticide described any one of (1) to (8) above.

DETAILED DESCRIPTION OF THE INVENTION

The type of the entomogenous fungus used in the present invention is not limited as long as the fungus can be parasitic on a termite and thereby kill the termite. Specific examples of the entomogenous fungus usable in the present invention include *Beauveria brongniartii, Beauveria bassiana, Beauveria amorpha, Metarhizium anisopliae*, and *Verticillium lecanii*. Among the above fungi, *Beauveria brongniartii* is most preferred because of its high activity against termites and quick effect. These fungi can be isolated from a body of an insect which died of the fungal parasity in the outdoors.

In the present specification, "the culture of entomogenous fungus" means a culture medium where an entomogenous fungus is grown, which comprises both the fungus and the medium. The media used herein are not limited as long as the fungi as mentioned above can grow thereon. Both solid and liquid media can be used, and the components contained therein are not particularly limited. Any known components as mentioned below can be used. Examples of carbon sources include glucose, fructose, saccharose, lactose, maltose, glycerol, starch, cellulose and molasses. Examples of nitrogen sources include ammonium sulfate, ammonium chloride, and ammonium nitrate. Inorganic salts other than nitrogen sources include potassium dihydrogen phosphate, magnesium sulfate, calcium sulfate, and potassium sulfate. Natural organic substances include extracts and pulverized powder of animal tissues, such as meat extract, fish meat extract, and silkworm pupa meal; extracts and pulverized powder of vegetable tissues, such as potato exudate powder, corn steep liquor, soybean oil, malt extract, and soybean powder; microorganism cells and extracts thereof, such as dry yeast, yeast extract, and polypeptone. A medium used in the present invention can be prepared by appropriately combining the above components. In order to prepare a solid medium, an appropriate amount of agar is added in a conventional manner. In the present invention, the culture of entomogenous fungus is prepared by growing an entomogenous fungus on the above-prepared medium usually at 25° C. for 3 to 7 days, but the culturing conditions are not limited to the above.

The target termites for the present invention are not limited. Examples include termites of *Coptotermes sp., Reticulitermes sp., Cryptotermes sp., Incisitermes sp., Macrotermes sp.*, and *Odontotermes sp.* More specific examples include termites of *Coptotermes formosanus, Reticulitermes speratus, Reticulitermes hesperus, Reticulitermes tibialis, Reticulitermes flavipes, Reticulitermes lucifungus, Reticulitermes santonensis, Cryptotermes domesticus*, and *Incisitermes minor*.

The entomogenous fungus and/or the culture thereof in the present invention can be used as a termiticide without any processing. Also, because the fungus used in the present invention may be germinated fungi or resting spores, it can be processed to have an appropriate application form. Examples of the application forms include powder, granules, tablets, liquid, aerosol, band, sheet, pellets, and cream. When solid forms, such as powder, granules, tablets, band, sheet and pellets, are used, it is preferred to use dry fungi to promote conidia.

The carriers used in the preparation of the above application forms are not limited, and any known carriers may be used. Examples of the carriers used in the present invention are as follows:

- examples of solid carriers used in the preparation of powder, granules, tablets and pellets include mineral powders (silicic acid, kaolin, active carbon, bentonite, montmorillonite, diatomaceous earth, talc, clay, calcium carbonate, alumina, acid clay, talc powder, agalmatolite powder, mica, silica sand, ammonium sulfate, etc.), vegetable powder (wood powder, soybean powder, wheat flour, tobacco powder, starch, crystalline cellulose, etc.) and clathrate compounds such as cyclodextrin;

examples of carriers used in the preparation of liquid and aerosol: water;

examples of carriers used in the preparation of band and sheet: synthetic fibers (polyethylene, nylon, polyvinyl chloride, polyvinylidene chloride, polyester, polypropylene, vinylone, etc.), and animal and vegetable fibers and inorganic fibers (resin, silk, cotton, wool, paper, cloth, non woven fabric, woven fabric, leather, aluminum, etc.); and examples of carriers used in the preparation of creams: hydrocarbons (liquid paraffin, vaseline, paraffin, etc.), silicones (dimethylsiloxane, colloidal silica, bentonite, etc.), alcohols (ethanol, stearyl alcohol, lauryl alcohol, etc.), polyhydric alcohols (polyethylene glycol, ethylene glycol, glycerol, etc.), carboxylic acids (lauric acid, stearic acid, etc.), and esters (beeswax, lanolin, etc.)

In the present invention, medium bases prepared by mixing the above carriers and medium components are preferably used.

The number of viable cells contained in each application form (cell density) is not particularly limited. It is preferably in the range of from $10^5$ to $10^9$ cells/$cm^2$ ($10^5$ to $10^9$ cells/g for solid forms), more preferably not less than $10^8$ cells/$cm^2$ (not less than $10^8$ cells/g for solid forms). *Beauveria brongniartii* can exhibit a high termiticidal activity even with a small cell density (about $10^6$ cells/$cm^2$, or $10^6$ cells/g for solid forms), which brings about various advantages. For example, this fungus requires a shorter period of time for culturing, and makes it possible to prepare compact application forms such as thinner sheet forms. The number of viable cells per unit area, unit volume, and unit weight (cell density) can be counted by the dilution plate technique.

The method for termite control of the present invention can be carried out by placing the above-mentioned termiticide of the present invention in the vicinity of a termite nest, or by directly spraying or injecting the termiticide of the present invention to the place infested with termites.

The present invention provides a simple and effective termite control without causing any harm to men and beasts.

EXAMPLES

The present invention will be further detailed by means of the following Examples, without intending to restrict the scope of the present invention thereto.

Example 1

*Beauveria brongniartii* was spread over the agar medium in a Petri dish and cultured at 25° C. for 5 days until cell density became $10^8$ cells/$cm^2$, the agar medium (manufactured by Nissui Pharmaceutical K.K.) containing 0.4% by weight of potato exudate powder, 2% by weight of glucose, and 1.5% by weight of agar. On the culture medium, 10 worker termites of *Coptotermes formosanus* were made to walk for 1 minute. Then the termites were transferred to another Petri dish containing filter paper and water-wetted cotton. The same experiment was repeated with another 3 groups of termites. With a total of 4 groups, the death number of the termites were counted at several time points after the walking on the termiticide. The results are shown in Table 1. As an untreated control group, 10 termites were made to walk on the same medium as the above except that *Beauveria brongniartii* was not grown thereon, treated and kept in the same way as above, and evaluated for mortality. The results are also shown in Table 1. In Table 1, the results are expressed in cumulative mortality (%) calculated from the death number at each measurement. *Beauveria brongniartii* used here was isolated from the body of long-horned beetles which died from infection with this fungus in the outdoors. The fungi used in the following examples were isolated in the same way.

TABLE 1

| Days after treatment | Cumulative mortality (%) Treated groups 1 | 2 | 3 | 4 | Untreated group |
|---|---|---|---|---|---|
| Day 0 | 0 | 0 | 0 | 0 | 0 |
| 1 | 0 | 0 | 0 | 10 | 0 |
| 2 | 50 | 10 | 10 | 10 | 0 |
| 3 | 70 | 30 | 20 | 20 | 0 |
| 4 | 90 | 40 | 40 | 40 | 0 |
| 5 | 100 | 60 | 40 | 40 | 0 |
| 6 | 100 | 100 | 100 | 60 | 0 |
| 7 | 100 | 100 | 100 | 100 | 0 |

As shown in Table 1, all the termites of *Coptotermes formosanus* in the treated groups in Example 1 died within 5 to 7 days. On the contrary, no death occurred before day 7 in the untreated control group. These findings demonstrate that termite *Coptotermes formosanus* dies from direct contact with the fungus and/or the culture thereof. This indicates that *Beauveria brongniartii* is usable as a termiticide.

Example 2

With *Beauveria bassiana*, the mortality of termite *Coptotermes formosanus* was evaluated in the same manner as in Example 1. Table 2 shows the results.

TABLE 2

| Days after treatment | Cumulative mortality (%) Treated groups 1 | 2 | 3 | 4 | Untreated group |
|---|---|---|---|---|---|
| Day 0 | 0 | 0 | 0 | 0 | 0 |
| 1 | 0 | 0 | 0 | 0 | 0 |
| 2 | 0 | 10 | 10 | 0 | 0 |
| 3 | 20 | 30 | 20 | 10 | 0 |
| 4 | 30 | 30 | 50 | 20 | 0 |
| 5 | 50 | 50 | 80 | 40 | 0 |
| 6 | 80 | 70 | 100 | 50 | 0 |
| 7 | 100 | 80 | 100 | 80 | 0 |
| 8 | 100 | 100 | 100 | 100 | 0 |

As shown in Table 2, all the termites of *Coptotermes formosanus* in the treated groups in Example 2 died within 6 to 8 days. On the contrary, no death occurred before day 8 in the untreated control group. These findings demonstrate that termite *Coptotermes formosanus* dies from direct contact with the fungus and/or the culture thereof. This indicates that *Beauveria bassiana* is usable as a termiticide.

Example 3

With *Metarhizium anisopliae*, the mortality of termite *Coptotermes formosanus* was evaluated in the same manner as in Example 1. Table 3 shows the results.

As shown in Table 3, all the termites in the treated groups in Example 3 were killed within 13 to 14 days. On the contrary, no death was found before day 14 in the untreated control group. These findings demonstrate that termite *Coptotermes formosanus* dies from direct contact with the fungus and/or the culture thereof. This indicates that *Metarhizium anisopliae* is usable as a termiticide.

TABLE 3

| Days after treatment | Cumulative mortality (%) | | | | Untreated group |
|---|---|---|---|---|---|
| | Treated groups | | | | |
| | 1 | 2 | 3 | 4 | |
| Day 0 | 0 | 0 | 0 | 0 | 0 |
| 1 | 0 | 0 | 0 | 0 | 0 |
| 2 | 0 | 0 | 0 | 0 | 0 |
| 3 | 0 | 0 | 10 | 0 | 0 |
| 4 | 0 | 10 | 20 | 10 | 0 |
| 5 | 10 | 10 | 20 | 20 | 0 |
| 6 | 20 | 30 | 30 | 20 | 0 |
| 7 | 20 | 30 | 30 | 20 | 0 |
| 8 | 30 | 30 | 50 | 30 | 0 |
| 9 | 30 | 40 | 50 | 40 | 0 |
| 10 | 50 | 60 | 60 | 40 | 0 |
| 11 | 70 | 80 | 80 | 60 | 0 |
| 12 | 90 | 90 | 80 | 80 | 0 |
| 13 | 100 | 100 | 100 | 90 | 0 |
| 14 | 100 | 100 | 100 | 100 | 0 |

Example 4

With *Verticillium lecanii*, the mortality of termite *Coptotermes formosanus* was evaluated in the same manner as in Example 1. Table 4 shows the results.

TABLE 4

| Days after treatment | Cumulative mortality (%) | | | | Untreated group |
|---|---|---|---|---|---|
| | Treated groups | | | | |
| | 1 | 2 | 3 | 4 | |
| Day 0 | 0 | 0 | 0 | 0 | 0 |
| 1 | 0 | 0 | 0 | 0 | 0 |
| 2 | 0 | 10 | 0 | 0 | 0 |
| 3 | 10 | 10 | 10 | 0 | 0 |
| 4 | 10 | 10 | 10 | 10 | 0 |
| 5 | 10 | 10 | 10 | 20 | 0 |
| 6 | 30 | 20 | 10 | 20 | 0 |
| 7 | 40 | 30 | 20 | 30 | 0 |
| 8 | 50 | 50 | 40 | 40 | 0 |
| 9 | 70 | 60 | 80 | 70 | 0 |
| 10 | 80 | 90 | 80 | 90 | 0 |
| 11 | 80 | 100 | 90 | 90 | 0 |
| 12 | 100 | 100 | 100 | 100 | 0 |

As shown in Table 4, all the termites of *Coptotermes formosanus* in the treated groups in Example 4 died within 11 to 12 days. On the contrary, no death occurred before day 12 in the untreated control group. These findings demonstrate that termite *Coptotermes formosanus* dies from direct contact with the fungus and/or the culture thereof. This indicates that *Verticillium lecanii* is usable as a termiticide.

Example 5

In a Petri dish where 10 normal worker termites of *Coptotermes formosanus* were kept with filter paper and water-wetted cotton, 3 dead bodies of the termites of *Coptotermes formosanus* which died from infection with *Beauveria brongniartii* in Example 1 were placed. Thereafter, the number of deaths in the 10 termites was evaluated at several time points. The same experiment was conducted with another 4 groups of normal termites, totaling 5 groups being evaluated for mortality at several time points after the exposure to the dead bodies. The results are shown in Table 5. A group of 10 termites were kept in the same way as the above without placing dead bodies of termites. This group was also evaluated for mortality as an untreated control group. Table 5 shows the results in cumulative mortality (%).

TABLE 5

| Days after treatment | Cumulative mortality (%) | | | | | Untreated group |
|---|---|---|---|---|---|---|
| | Treated groups | | | | | |
| | 1 | 2 | 3 | 4 | 5 | |
| Day 0 | 0 | 0 | 0 | 0 | 0 | 0 |
| 1 | 0 | 10 | 10 | 10 | 0 | 0 |
| 2 | 0 | 10 | 10 | 10 | 20 | 0 |
| 3 | 0 | 10 | 20 | 10 | 20 | 0 |
| 4 | 0 | 30 | 20 | 20 | 40 | 0 |
| 5 | 0 | 30 | 20 | 20 | 50 | 0 |
| 6 | 30 | 70 | 30 | 30 | 60 | 0 |
| 7 | 100 | 100 | 50 | 50 | 70 | 10 |
| 8 | 100 | 100 | 50 | 50 | 80 | 10 |
| 9 | 100 | 100 | 50 | 50 | 80 | 10 |
| 10 | 100 | 100 | 70 | 60 | 80 | 10 |
| 11 | 100 | 100 | 90 | 100 | 100 | 10 |
| 12 | 100 | 100 | 100 | 100 | 100 | 10 |

As shown in Table 5, even if there is no direct exposure to the fungus and/or the culture thereof, normal termites can be killed by being infected with the fungus by making contact with the dead body of a termite that dies from the fungus.

Example 6

On an agar culture medium where *Beauveria brongniartii* was grown in the same manner as in Example 1, smoky-brown cockroach (*Periplaneta fuliginosa*), German cockroach (*Blattella germanica*), termite (*Coptotermes formosanus*), pill wood louse (*Armadillidium vulgare*), sow bug (*Porcellio scaber*), queenless ant (*Pristomyrmex pungens*), large centipede (*Scolopendra subspinipes mutilans*), and shield centipede (*Thereuonema hilgendorfi*) were made to have a 5-minute free walk. Each kind of the test insects was kept in a polyethylene cup with water-wetted cotton and feed, and observed for 14 days. The results of the observation are shown in Table 6. An untreated control group was prepared for each kind of the test insects by following the same procedures as the above except that an agar medium which did not grow the fungus was used. The results are shown in Table 7.

TABLE 6

| Days after treatment | Cumulative number of deaths | | | |
|---|---|---|---|---|
| | Smoky-brown cockroach (*Periplaneta fuliginosa*) | German cockroach (*Blattella germanica*) | Termite (*Coptotermes formosanus*) | Pill wood louse (*Armadillidium vulgare*) |
| Day 0 | 0 | 0 | 0 | 0 |
| 1 | 1 | 0 | 0 | 1 |
| 2 | 1 | 0 | 0 | 1 |
| 3 | 1 | 1 | 6 | 1 |
| 4 | 1 | 1 | 14 | 1 |
| 5 | 1 | 1 | 29 | 1 |
| 6 | 1 | 1 | 30 | 1 |
| 7 | 1 | 1 | 30 | 1 |
| 8 | 1 | 1 | 30 | 1 |
| 9 | 1 | 1 | 30 | 1 |
| 10 | 1 | 1 | 30 | 1 |
| 13 | 1 | 1 | 30 | 1 |
| 14 | 1 | 2 | 30 | 1 |
| No. of test insects | 10 | 10 | 30 | 20 |

| Days after treatment | Cumulative number of deaths | | | |
|---|---|---|---|---|
| | Sow bug (*Porcellio scaber*) | Queenless ant (*Pristomyrmex pungens*) | Large Centipede (*Scolopendra subspinipes mutilans*) | Shield centipede (*Thereuonema hilgendorfi*) |
| Day 0 | 0 | 0 | 0 | 0 |
| 1 | 1 | 0 | 0 | 0 |
| 2 | 1 | 0 | 0 | 0 |
| 3 | 1 | 0 | 0 | 0 |
| 4 | 1 | 1 | 0 | 0 |
| 5 | 1 | 2 | 0 | 0 |
| 6 | 1 | 2 | 0 | 0 |
| 7 | 1 | 2 | 0 | 0 |
| 8 | 1 | 2 | 0 | 0 |
| 9 | 1 | 2 | 0 | 0 |
| 10 | 1 | 3 | 0 | 0 |
| 13 | 1 | 3 | 0 | 0 |
| 14 | 1 | 3 | 0 | 0 |
| No. of test insects | 20 | 50 | 10 | 10 |

TABLE 7

| Days after treatment | Smoky-brown cockroach (*Periplaneta fuliginosa*) | German cockroach (*Blattella germanica*) | Termite (*Coptotermes formosanus*) | Pill wood louse (*Armadillidium vulgare*) |
|---|---|---|---|---|
| Day 0 | 0 | 0 | 0 | 0 |
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 1 | 0 | 0 |
| 6 | 0 | 1 | 0 | 1 |
| 7 | 0 | 1 | 0 | 1 |
| 8 | 0 | 1 | 0 | 1 |
| 9 | 0 | 1 | 0 | 1 |
| 10 | 0 | 1 | 0 | 1 |
| 13 | 0 | 1 | 0 | 1 |
| 14 | 0 | 1 | 0 | 1 |
| No. of test insects | 10 | 10 | 30 | 20 |

TABLE 7-continued

| | Cumulative number of deaths | | | |
|---|---|---|---|---|
| Days after treatment | Sow bug (Porcellio scaber) | Queenless ant (Pristomyrmex pungens) | Large Centipede (Scolopendra subspinipes mutilans) | Shield centipede (Thereuonema hilgendorfi) |
| Day 0 | 0 | 0 | 0 | 0 |
| 1 | 0 | 0 | 0 | 0 |
| 2 | 1 | 1 | 0 | 0 |
| 3 | 1 | 1 | 0 | 0 |
| 4 | 1 | 1 | 0 | 0 |
| 5 | 1 | 1 | 0 | 0 |
| 6 | 1 | 1 | 0 | 0 |
| 7 | 1 | 2 | 0 | 0 |
| 8 | 1 | 2 | 0 | 0 |
| 9 | 1 | 2 | 0 | 0 |
| 10 | 1 | 2 | 0 | 0 |
| 13 | 1 | 2 | 0 | 0 |
| 14 | 1 | 3 | 0 | 0 |
| No. of test insects | 20 | 50 | 10 | 10 |

As shown in Tables 6 and 7, the termiticide of the present invention was highly specific to termite *Coptotermes formosanus* and did not show lethal effect to other test insects. This indicates that the termiticide of the present invention is excellent in that it gives little damages to the environment with giving no harms to other living things.

Example 7

In a basal liquid medium which was prepared by adding 40 g of glucose, 10 g of peptone, and 2 g of yeast extract to 1 L of water, *Beauveria brongniartii* was grown at 25° C. for 2 weeks. Separately, 2 L of water was added to 1 kg of wheat bran and sterilized in an autoclave at 121° C. for 20 minutes, to which 1 to 5 mL of the above liquid culture medium of *Beauveria brongniartii* was added and cultured at 25° C. for 2 weeks. Then the culture was air-dried to obtain a powder with cell density of $10^8$ cells/g.

The powder thus obtained was sprinkled in an amount of 300 g in an outdoor termite nest where not less than 5000 active termites of *Coptotermes formosanus* inhabited. The area sprinkled with the powder was referred to as the treated area. Thereafter, the termites in the nest were periodically observed. The results are shown in Table 8. An untreated area was prepared in the same manner as the above except that the culture medium did not grow *Beauveria brongniartii*, and the termites in the nest were observed. The results are shown in Table 8.

TABLE 8

| | No. of active termites | | | |
|---|---|---|---|---|
| Days after treatment | Treated area 1 | Treated area 2 | Treated area 3 | Untreated area |
| Day 0 | +++ | +++ | +++ | +++ |
| 5 | +++ | +++ | +++ | +++ |
| 10 | +++ | +++ | +++ | +++ |
| 15 | +++ | +++ | ++ | +++ |
| 20 | +++ | ++ | ++ | +++ |
| 25 | ++ | ++ | ++ | +++ |
| 30 | ++ | ++ | + | +++ |
| 35 | + | + | + | +++ |
| 40 | – | + | + | +++ |
| 45 | – | – | – | +++ |

Note: +++ indicates not less than 5000 active termites; ++, 500 to 4999; +, less than 500; and –, 0.

As shown in Table 8, it was found that all the termites in the outdoor nest can be eradicated by sprinkling the culture of the fungus (the powder) on the nest. This demonstrates the high efficacy of the present invention for termite control.

Example 8

From an active nest in the outdoors where not less than 1000 termites of *Coptotermes formosannus* inhabited, 300 termites (workers and soldiers) were collected. These termites were made to walk for 10 minutes on the agar culture medium of *Beauveria brongniartii* in the same manner as in Example 1 and returned to the nest where they were collected. The nest was referred to as "the treated area." The termites in the nest were observed periodically. The results of the observation are shown in Table 9. An untreated area was prepared by following the same procedures as the above except that termites were made to walk on the agar medium where no fungus was grown, and the termites in the nest were observed. The results are shown in Table 9.

TABLE 9

| | No. of active termites | | | |
|---|---|---|---|---|
| Days after treatment | Treated area 1 | Treated area 2 | Treated area 3 | Untreated area |
| 0 | +++ | +++ | +++ | +++ |
| 5 | +++ | +++ | +++ | +++ |
| 10 | +++ | +++ | +++ | +++ |
| 15 | ++ | +++ | ++ | +++ |
| 20 | ++ | ++ | + | +++ |
| 25 | + | ++ | + | +++ |
| 30 | – | + | – | +++ |
| 35 | – | – | – | +++ |

Note: +++ indicates not less than 1000 active termites; ++, 300 to 999; +, less than 300; and –, 0.

As shown in Table 9, according to the method of the present invention, treatment of only a part of termites in the nest with the culture of the fungus resulted in eradication of all the termites in the nest, indicating marked efficacy of the present invention for termite control.

Example 9

In the same manner as in Example 1, 10 worker termites of *Coptotermes formosannus* were made to walk for 10 minutes on an agar medium where each of the fungi was grown. Then, these test termites were placed in a polyethylene cup where 50 normal termites of *Coptotermes formosannus* (workers and soldiers) were kept with wood chips and water-wetted cotton. The number of days needed before all the termites in the cup died was determined. The same experiment was conducted with another 4 groups, involving 5 groups in total for each fungus. The results are shown in Table 10. An untreated group for each fungus was prepared by following the same procedures as the above except that an agar medium did not grow any fungus. The results in the untreated group are also shown in Table 10.

TABLE 10

| Kind of fungi | Days needed before 100% mortality was achieved | | | | | | |
|---|---|---|---|---|---|---|---|
| | 1 | 2 | 3 | 4 | 5 | Average | ** |
| *Beauveria brongniartii* | 5 | 7 | 7 | 6 | 5 | 6 | — |
| *Beauveria bassiana* | 10 | 8 | 8 | 9 | 12 | 9.4 | — |
| *Beauveria amorpha* | 15 | 16 | 18 | 17 | 14 | 16 | — |
| *Metarhizium anisopliae* | 18 | 14 | 15 | 17 | 15 | 15.8 | — |
| *Verticillium lecanii* | 19 | 15 | 17 | 21 | 18 | 18 | — |

**: Untreated group

As shown in Table 10, treatment of only one fifth the termites of *Coptotermes formosannus* with each of the fungi resulted in eradication of the whole group. There was no death in each untreated group. Therefore, the termiticide of the present invention can effectively control termites even if all the termites do not make direct contact with the termiticide. With *Beauveria brongniartii*, the number of days needed before 100% death of the termites was achieved was the shortest, indicating the highest termiticidal efficacy of the fungus.

Example 10

With termite *Reticulitermes speratus*, the number of deaths was evaluated in the same manner as in Example 1 where termites were treated with *Beauveria brongniartii*. The results are shown in Table 11.

TABLE 11

| Days after treatment | Cumulative mortality (%) | | | Untreated group |
|---|---|---|---|---|
| | Treated groups | | | |
| | 1 | 2 | 3 | |
| Day 0 | 0 | 0 | 0 | 0 |
| 1 | 0 | 0 | 0 | 0 |
| 2 | 10 | 0 | 10 | 0 |
| 3 | 10 | 0 | 10 | 0 |
| 4 | 40 | 10 | 30 | 0 |
| 5 | 40 | 40 | 40 | 0 |
| 6 | 70 | 50 | 50 | 0 |
| 7 | 90 | 60 | 80 | 0 |
| 8 | 100 | 70 | 90 | 0 |
| 9 | 100 | 80 | 100 | 0 |
| 10 | 100 | 100 | 100 | 0 |

As shown in Table 11, all the termites of *Reticulitermes speratus* in the treated groups died within 8 to 10 days. On the contrary, no death occurred before day 10 in the untreated group, indicating that *Beauveria brongniartii* can be used as a termiticide.

Example 11

With termite *Reticulitermes speratus*, the number of death was evaluated in the same manner as in Example 2 where the termites were treated with *Beauveria bassiana*. The results are shown in Table 12.

TABLE 12

| Days after treatment | Cumulative mortality (%) | | | Untreated group |
|---|---|---|---|---|
| | Treated groups | | | |
| | 1 | 2 | 3 | |
| Day 0 | 0 | 0 | 0 | 0 |
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 10 | 20 | 0 | 0 |
| 6 | 20 | 30 | 10 | 0 |
| 7 | 30 | 30 | 10 | 0 |
| 8 | 30 | 40 | 20 | 0 |
| 9 | 50 | 40 | 30 | 0 |
| 10 | 60 | 40 | 30 | 0 |
| 11 | 60 | 40 | 30 | 0 |
| 12 | 60 | 50 | 40 | 0 |
| 13 | 60 | 50 | 40 | 0 |
| 14 | 60 | 50 | 40 | 0 |

As shown in Table 12, the cumulative mortality at day 14 was 40 to 60% in the treated groups, while no death occurred in the untreated group.

Example 12

With termite *Reticulitermes speratus*, the number of deaths was evaluated in the same manner as in Example 3 where the termites were treated with *Metarhizium anisopliae*. The results are shown in Table 13.

TABLE 13

| Days after treatment | Cumulative mortality (%) | | | Untreated group |
|---|---|---|---|---|
| | Treated groups | | | |
| | 1 | 2 | 3 | |
| Day 0 | 0 | 0 | 0 | 0 |
| 1 | 0 | 0 | 0 | 0 |
| 2 | 0 | 0 | 0 | 0 |
| 3 | 10 | 10 | 10 | 0 |
| 4 | 20 | 30 | 20 | 0 |
| 5 | 30 | 30 | 40 | 0 |
| 6 | 30 | 60 | 40 | 0 |
| 7 | 30 | 60 | 40 | 0 |
| 8 | 30 | 80 | 40 | 0 |
| 9 | 60 | 80 | 60 | 0 |
| 10 | 70 | 90 | 90 | 0 |
| 11 | 90 | 100 | 100 | 0 |
| 12 | 100 | 100 | 100 | 0 |

As shown in Table 13, all the termites of *Reticulitermes speratus* in the treated groups died within 11 to 12 days. On the contrary, no death occurred before day 12 in the untreated group. These findings show that direct contact with the fungus and/or the culture thereof causes the termites to die. Therefore, though less effective than *Beauveria brongniartii* in Example 10, *Metarhizium anisopliae* can also be used as a termiticide.

Example 13

With termite *Reticulitermes speratus*, the number of deaths was evaluated in the same manner as in Example 4 where the termites were treated with *Verticillium lecanii*. The results are shown in Table 14.

TABLE 14

| Days after treatment | Cumulative mortality (%) Treated groups | | | Untreated group |
|---|---|---|---|---|
| | 1 | 2 | 3 | |
| Day 0 | 0 | 0 | 0 | 0 |
| 1 | 0 | 0 | 0 | 0 |
| 2 | 0 | 0 | 0 | 0 |
| 3 | 0 | 0 | 0 | 0 |
| 4 | 10 | 0 | 10 | 0 |
| 5 | 10 | 0 | 10 | 0 |
| 6 | 30 | 10 | 30 | 0 |
| 7 | 30 | 10 | 30 | 0 |
| 8 | 30 | 10 | 30 | 0 |
| 9 | 30 | 10 | 40 | 0 |
| 10 | 30 | 10 | 40 | 0 |
| 11 | 30 | 10 | 40 | 0 |
| 12 | 30 | 10 | 40 | 0 |
| 13 | 30 | 20 | 40 | 0 |
| 14 | 30 | 20 | 40 | 0 |

As shown in Table 14, the cumulative mortality at day 14 was 20 to 40% in the treated groups, while no death occurred in the untreated group before day 14.

Example 14

With termite *Coptotermes formosanus*, the number of deaths was evaluated in the same manner as in Example 1 except that the termites were treated with *Beauveria amorpha*. The results are shown in Table 15.

TABLE 15

| Days after treatment | Cumulative mortality (%) Treated groups | | | | Untreated group |
|---|---|---|---|---|---|
| | 1 | 2 | 3 | 4 | |
| Day 0 | 0 | 0 | 0 | 0 | 0 |
| 1 | 0 | 0 | 0 | 0 | 0 |
| 2 | 0 | 0 | 0 | 0 | 0 |
| 3 | 10 | 0 | 0 | 0 | 0 |
| 4 | 20 | 10 | 10 | 20 | 0 |
| 5 | 20 | 30 | 30 | 30 | 0 |
| 6 | 40 | 30 | 30 | 40 | 0 |
| 7 | 60 | 30 | 50 | 40 | 0 |
| 8 | 80 | 60 | 50 | 60 | 0 |
| 9 | 90 | 80 | 60 | 70 | 0 |
| 10 | 90 | 80 | 80 | 90 | 0 |
| 11 | 100 | 80 | 90 | 100 | 0 |
| 12 | 100 | 100 | 100 | 100 | 0 |

As shown in Table 15, all the termites of *Coptotermes formosanus* in the treated group died within 11 to 12 days, while no death occurred in the untreated group before day 12. These findings show that direct contact with the fungus and/or the culture thereof causes the termites to die. Though *Beauveria amorpha* is less effective in killing the termites than *Beauveria brongniartii* (Example 1), *Beauveria amorpha* can also be used as a termiticide.

Example 15

Each of *Beauveria brongniartii*, *Beauveria bassiana*, and *Beauveria amorpha* was spread over an agar medium in a Petri dish and cultured at 25° C., the agar medium (manufactured by Nissui Pharmaceutical K.K.) containing 0.4% by weight of potato exudate powder, 2% by weight of glucose, and 1.5% by weight of agar. The duration of the culture (number of days) was controlled in order to make 3 levels of cell density, i.e. $10^6$, $10^7$, and $10^8$ cells/cm$^2$. The experiment was conducted in a similar way to Example 1. The results are shown in Tables 16 to 18. Cell density was obtained by counting the number of cells per unit area using the dilution plate technique.

TABLE 16

| Days after treatment | Cumulative mortality (%) | | |
|---|---|---|---|
| | $10^6$* | $10^7$* | $10^8$* |
| Day 0 | 0 | 0 | 0 |
| 1 | 0 | 0 | 0 |
| 2 | 0 | 0 | 10 |
| 3 | 0 | 10 | 30 |
| 4 | 0 | 30 | 50 |
| 5 | 20 | 40 | 70 |
| 6 | 30 | 60 | 90 |
| 7 | 30 | 80 | 100 |
| 8 | 50 | 100 | 100 |
| 9 | 70 | 100 | 100 |
| 10 | 70 | 100 | 100 |
| 15 | 90 | 100 | 100 |
| 20 | 100 | 100 | 100 |

Treated with *Beauveria brongniartii*.
*cell density (cells/cm$^2$)

TABLE 17

| Days after treatment | Cumulative mortality (%) | | |
|---|---|---|---|
| | $10^6$* | $10^7$* | $10^8$* |
| Day 0 | 0 | 0 | 0 |
| 1 | 0 | 0 | 0 |
| 2 | 0 | 0 | 10 |
| 3 | 0 | 0 | 30 |
| 4 | 0 | 0 | 30 |
| 5 | 0 | 10 | 50 |
| 6 | 0 | 10 | 70 |
| 7 | 10 | 20 | 80 |
| 8 | 10 | 20 | 100 |
| 9 | 10 | 20 | 100 |
| 10 | 20 | 30 | 100 |
| 15 | 20 | 40 | 100 |
| 20 | 20 | 40 | 100 |

Treated with *Beauveria bassiana*.
*cell density (cells/cm$^2$)

TABLE 18

| Days after treatment | Cumulative mortality (%) | | |
|---|---|---|---|
| | $10^6$* | $10^7$* | $10^8$* |
| Day 0 | 0 | 0 | 0 |
| 1 | 0 | 0 | 0 |
| 2 | 0 | 0 | 0 |
| 3 | 0 | 0 | 10 |
| 4 | 0 | 0 | 30 |
| 5 | 0 | 0 | 40 |
| 6 | 0 | 0 | 50 |
| 7 | 0 | 10 | 60 |
| 8 | 0 | 10 | 60 |
| 9 | 10 | 10 | 80 |
| 10 | 10 | 10 | 90 |
| 15 | 10 | 20 | 100 |
| 20 | 20 | 30 | 100 |

Treated with *Beauveria amorpha*.
*cell density (cells/cm$^2$)

As shown in Tables 16 to 18, when *Beauveria brongniartii* was used, 100% mortality of termite *Coptotermes formosanus* was achieved even when the cell density of the fungus was low ($10^6$ cells/cm$^2$). In case of *Beauveria*

*bassiana* or *Beauveria amorpha*, 100% mortality could not be achieved with low cell densities of not less than $10^8$ cells/cm$^2$. Thus, since *Beauveria brongniartii* can achieve 100% mortality with a low cell density, this fungus is the most effective for termite control.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for termite control comprising the step of contacting a termiticide comprising *Beauveria brongniartii* and/or culture thereof with a target termite which is susceptible to treatment by said *Beauveria brongniartii*.

2. The method according to claim 1, wherein the *Beauveria brongniartii* is in the state of germination or resting spore.

3. The method according to claim 1, wherein the *Beauveria brongniartii* and/or the culture thereof are contained in an application form selected from the group consisting of powder, granule, tablet, liquid, aerosol, band, sheet, pellets, and cream.

4. The method according to claim 1, wherein a target termite is selected from the group consisting of *Coptotermes formosanus*, *Reticulitermes speratus*, *Reticulitermes hesperus*, *Reticulitermes tibialis*, *Reticulitermes flavipes*, *Reticulitermes lucifugus*, *Reticulitermes santonensis*, *Cryptotermes domesticus*, and *Incisitermes minor*.

5. The method according to claim 1, further comprising the step of contacting with living target termites dead bodies of the target termites which have previously died from contact with the termiticide.

6. The method according to claim 1, wherein cell density of *Beauveria brongniartii* in the application form is $10^5$ to $10^9$ cells/cm$^2$ or $10^5$ to $10^9$ cells/g.

7. The method according to claim 1, wherein cell density of *Beauveria brongniartii* in the application form is about $10^6$ cells/cm$^2$ or about $10^6$ cells/g.

8. The method according to claim 1, wherein a target termite is selected from the group consisting of *Coptotermes sp.*, *Reticulitermes sp.*, *Cryptotermes sp.*, *Incisitermes sp.*, *Macrotermes sp.*, and *Odontotermes sp.*

9. The method of claim 1, wherein said termite is *Coptotermes sp.*

10. The method of claim 1, wherein said termite is *Reticulitermes sp.*

11. The method of claim 1, wherein said termite is *Coptotermes formosanus*.

12. The method of claim 1, wherein said termite is *Reticulitermes speratus*.

13. The method of claim 1, wherein said termiticide is placed in the vicinity of a termite nest.

14. The method of claim 1, wherein said termiticide is directly sprayed or injected to a place infested with termites.

* * * * *